US00PP16972P2

(12) United States Plant Patent
Oudshoorn

(10) Patent No.: US PP16,972 P2
(45) Date of Patent: Aug. 8, 2006

(54) ***SEDUM* PLANT NAMED 'NOVEM'**

(50) Latin Name: *Sedum telephium*
Varietal Denomination: Novem

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/141,555

(22) Filed: May 31, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Sedum* plant named 'Novem', characterized by its upright plant habit; freely basal branching growth habit; and purple-colored flowers.

1 Drawing Sheet

Botanical designation: *Sedum telephium.*
Cultivar denomination: 'Novem'.

BACKGROUND OF THE INVENTION

The present Invention relates to a new and distinct cultivar of *Sedum* plant, botanically known as *Sedum telephium*, and hereinafter referred to by the name 'Novem'.

The new *Sedum* is a product of a planned breeding program conducted by the Inventor in Rijpwetering, The Netherlands. The objective of the breeding program is to develop new compact *Sedum* cultivars with uniform growth habit and attractive flower coloration.

The new *Sedum* originated from a cross-pollination made by the Inventor in 2002 of the *Sedum telephium* cultivar Purple Emperor, not patented, as the female, or seed, parent with the *Sedum telephium* cultivar Herbstfreude, not patented, as the male, or pollen, parent. The new *Sedum* was discovered and selected by the Inventor as a single flowering plant within the progeny of the stated cross-pollination grown in a controlled environment in Rijpwetering, The Netherlands in 2003.

Asexual reproduction of the new cultivar by terminal cuttings taken at Rijpwetering, The Netherlands, since 2003, has shown that the unique features of this new *Sedum* are stable and reproduced true to type in successive generations.

SUMMARY OF THE INVENTION

Plants of the cultivar Novem have not been observed under all possible environmental conditions. The phenotype may vary somewhat with variations in environment such as temperature and light intensity without, however, any variance in genotype.

The following traits have been repeatedly observed and are determined to be the unique characteristics of 'Novem'. These characteristics in combination distinguish 'Novem' as a new and distinct cultivar:

1. Upright plant habit.
2. Freely basal branching growth habit.
3. Purple-colored flowers.

Plants of the new *Sedum* can be compared to plants of the female parent, the cultivar Purple Emperor. Plants of the new *Sedum* differ from plants of the cultivar Purple Emperor primarily in plant height as plants of the new *Sedum* are more compart than plants of the cultivar Purple Emperor.

Plants of the new *Sedum* can be compared to plants of the male parent, the cultivar Herbstfreude. Plants of the new *Sedum* differ from plants of the cultivar Herbstfreude primarily in plant height as plants of the new *Sedum* are more compact than plants of the cultivar Herbstfreude.

Plants of the new *Sedum* can also be compared to plants of the *Sedum telephium* cultivar Lajos, disclosed in U.S. Plant Pat. No. 14,421. In side-by-side comparisons conducted in Rijpwetering, The Netherlands, plants of the new *Sedum* differed from plants of the cultivar Lajos in the following characteristics:

1. Plants of the new *Sedum* were more compact than plants of the cultivar Lajos.
2. Plants of the new *Sedum* and the cultivar Lajos differed in leaf coloration as plants of the Lajos had variegated leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Sedum*. The photograph is a side perspective view of a typical plant of 'Novem' grown in a container.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late summer in an outdoor nursery in Rijpwetering, The Netherlands for about one year. During the production of the plants, day temperatures ranged from 14 to 32° C. and night temperatures ranged from 7 to 18° C.

Botanical classification: *Sedum telephium* cultivar Novem.

Parentage:

*Female parent.*—*Sedum telephium* cultivar Purple Emperor, not patented.

*Male parent.*—*Sedum telephium* cultivar Herbstfreude, not patented.

Propagation:

*Type cutting.*—Terminal vegetative cuttings.

*Time to produce a rooted young plant.*—About three months at 18° C.

*Root description.*—Fine, fleshy; light brown in color.

*Rooting habit.*—Freely branching.

Plant description:

*Form/growth habit.*—Upright plant form; inverted triangle. Freely basal branching, about four basal branches per plant; moderately vigorous growth habit. Numerous single flowers arranged in terminal and axillary cymes.

*Plant height.*—About 51 cm.

*Plant width.*—About 32 cm.

*Branch description.*—Length: About 39 cm. Diameter: About 7 mm. Internode length: About 4.3 cm. Strength: Moderately strong. Aspect: Mostly upright. Texture: Smooth, glabrous; succulent. Color: 184C; towards the base, 182B to 182C.

*Foliage description.*—Arrangement: Opposite, simple; sessile. Length: About 5.8 cm. Width: About 3.1 cm. Shape: Ovate. Apex: Bluntly acute. Base: Cordate; clasping. Margin: Irregularly serrate. Texture, upper and lower surfaces: Smooth, glabrous; succulent. Venation pattern: Pinnate; arcuate. Color: Developing foliage, upper surface: Between 186A and 200A. Developing foliage, lower surface: N187C to 147A to 148A. Fully expanded foliage, upper surface: Between 186A and 200A; venation, similar to lamina. Fully expanded foliage, lower surface: 148A; towards the apical margin, N187A to N187B; venation, 146A to 146B tinted with 187A to 187B.

Flower description:

*Flower arrangement and shape.*—Small single star-shaped flowers arranged in terminal and axillary compound cymes; cymes roughly hemispherical. Flowers face mostly upright. Freely flowering, about 110 flowers and flower buds per lateral branch.

*Natural flowering season.*—Flowering continuous from August through September in The Netherlands.

*Flower longevity on the plant.*—Individual last about two weeks on the plant. Flowers persistent.

*Fragrance.*—None detected.

*Flower buds.*—Length: About 4 mm. Diameter: About 2 mm. Shape: Ovoid. Color: 182A; towards the apex, 183B to 183C.

*Inflorescence diameter.*—About 8.8 cm.

*Inflorescence height.*—About 4.7 cm.

*Flowers.*—Diameter: About 7 mm. Depth (height): About 5 mm.

*Petals.*—Arrangement: Five, fused at base. Length: About 4 mm. Width: About 1.5 mm. Shape: Ovate. Apex: Acute. Margin: Entire. Texture, upper and lower surfaces: Smooth, glabrous. Color: When opening, upper and lower surfaces: 187D; towards the base, 186D; color becoming closer to 183A to 183B with development. Fully opened, upper and lower surfaces: 187D; towards the base, 186D.

*Calyx.*—Arrangement: Five sepals fused at the base; campanulate. Length: About 1 mm. Diameter: About 0.7 mm. Sepal shape: Narrowly ovate. Sepal apex: Acute. Sepal texture, upper and lower surfaces: Smooth, glabrous. Sepal color, upper surface: 177C. Sepal color, upper surface: 177C; heavily spotted with 185C.

*Peduncles.*—Length: About 12 cm. Diameter: About 4 mm. Strength: Moderately strong. Texture: Smooth, glabrous. Aspect: Erect to about 30° from vertical. Color: 184C.

*Pedicels.*—Length: About 5 mm. Diameter: About 1 mm. Strength: Moderately strong. Texture: Smooth, glabrous. Aspect: Erect to about 45° from the stem axis. Color: 177C; heavily spotted with 185C.

*Reproductive organs.*—Stamens: Quantity per flower/arrangement: About ten; five stamens at base of petals; other five, free. Anther shape: Broadly oblong; flattened. Anther length: About 0.4 mm. Anther color: 8B to 8C. Filament length: About 3 mm. Filament color: N155B. Pollen amount: Scarce. Pollen color: 6C. Pistils: Quantity/arrangement: Five per flower; prominent; fused at the base; star-shaped. Pistil length: About 3 mm. Stigma shape: Rounded; minute. Stigma color: 186A. Style length: About 2.5 mm. Style color: 186C to 186D. Ovary color: 186C to 186D or lighter.

*Seed/fruit.*—Seed and fruit production has not been observed.

Disease/pest resistance: Plants of the new *Sedum* have not been noted to be resistant to pathogens and pests common to *Sedum*.

Weather tolerance: Plants of the new *Sedum* have exhibited good tolerance to rain and wind and have been observed to tolerate temperatures from −10 to 35° C.

It is claimed:

1. A new and distinct cultivar of *Sedum* plant named 'Novem', as illustrated and described.

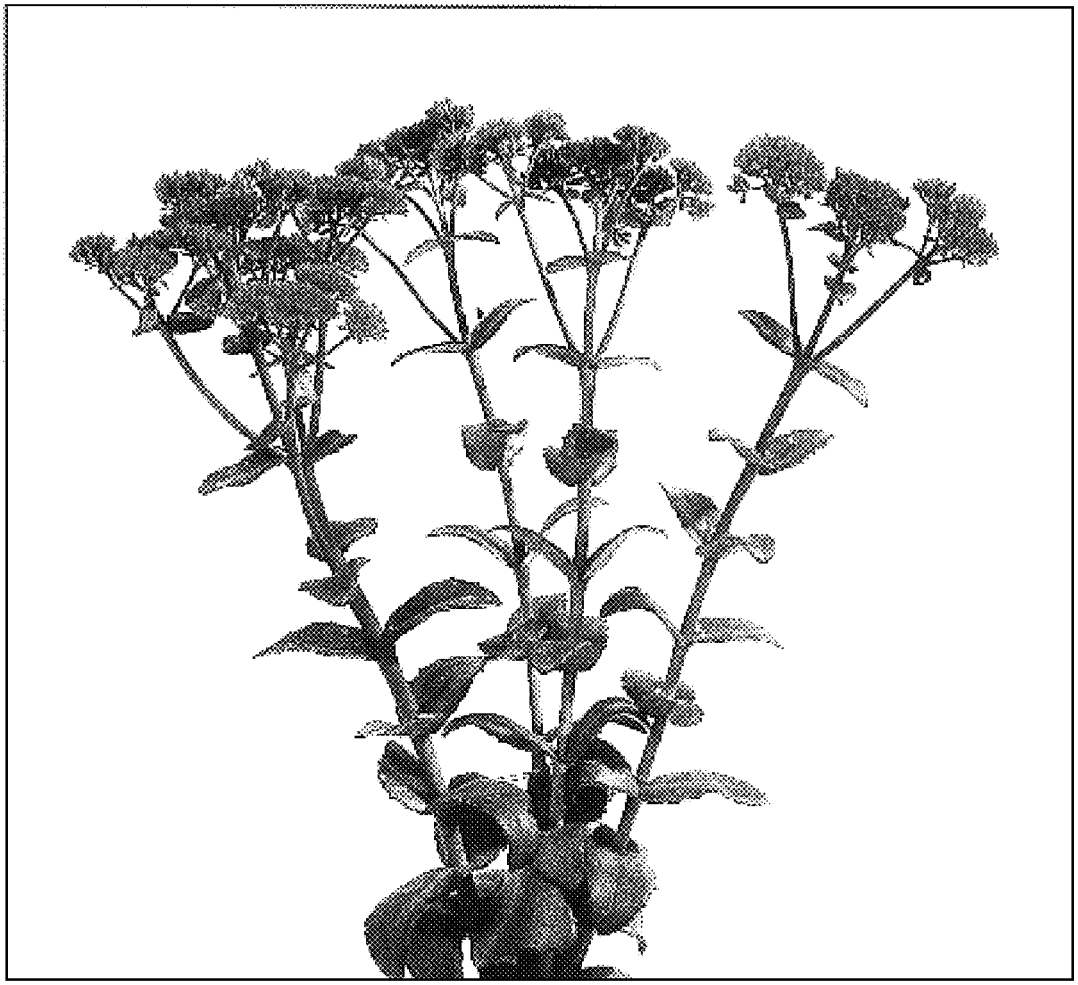

* * * * *